United States Patent
Shimada

(10) Patent No.: US 9,855,172 B2
(45) Date of Patent: Jan. 2, 2018

(54) METHOD FOR PRODUCING DISPOSABLE WORN ARTICLE AND WELDING DEVICE USED IN SAME

(71) Applicant: ZUIKO CORPORATION, Settsu-shi, Osaka (JP)

(72) Inventor: Takahiro Shimada, Osaka (JP)

(73) Assignee: ZUIKO CORPORATION, Settsu-Shi, Osaka (JP)

( * ) Notice: Subject to any disclaimer, the term of this patent is extended or adjusted under 35 U.S.C. 154(b) by 283 days.

(21) Appl. No.: 14/650,629

(22) PCT Filed: Dec. 19, 2013

(86) PCT No.: PCT/JP2013/007469
§ 371 (c)(1),
(2) Date: Jun. 9, 2015

(87) PCT Pub. No.: WO2014/097634
PCT Pub. Date: Jun. 26, 2014

(65) Prior Publication Data
US 2015/0320607 A1    Nov. 12, 2015

(30) Foreign Application Priority Data
Dec. 21, 2012    (JP) .................................. 2012-280108

(51) Int. Cl.
*B32B 37/00*    (2006.01)
*A61F 13/15*    (2006.01)
(Continued)

(52) U.S. Cl.
CPC .. *A61F 13/15699* (2013.01); *A61F 13/15739* (2013.01); *A61F 13/15756* (2013.01);
(Continued)

(58) Field of Classification Search
CPC .............. B29C 65/086; B29C 65/7891; B29C 65/8253; B29C 66/1122; B29C 66/431;
(Continued)

(56) References Cited

U.S. PATENT DOCUMENTS

| 5,246,433 A | 9/1993 | Hasse et al. |
| 5,254,194 A | 10/1993 | Ott et al. |

(Continued)

FOREIGN PATENT DOCUMENTS

| JP | 2-18036 | 1/1990 |
| JP | 3-126529 | 5/1991 |

(Continued)

OTHER PUBLICATIONS

International Search Report dated Mar. 25, 2014.
Chinese Office Action dated Dec. 28, 2016.

*Primary Examiner* — James D Sells
(74) *Attorney, Agent, or Firm* — Gerald E. Hespos; Michael J. Porco; Matthew T. Hespos

(57) ABSTRACT

Partly-finished products having side panel pieces are supplied intermittently to places between welding surfaces of a horn and a rotating anvil. Thus, the side pieces of the partly-finished products, are welded continuously to each other with a predetermined pattern. The welding surfaces of the anvil are provided over an entire circumference about a rotating shaft so that the interval between the welding surfaces of the anvil and the horns is maintained at an interval at which the respective side panel pieces are continuously weldable to each other with the predetermined pattern regardless of a rotating position of the anvil.

4 Claims, 8 Drawing Sheets

(51) Int. Cl.
| | |
|---|---|
| *B32B 37/20* | (2006.01) |
| *B32B 37/06* | (2006.01) |
| *B32B 37/10* | (2006.01) |
| *A61F 13/49* | (2006.01) |
| *B29C 65/08* | (2006.01) |
| *B29C 65/78* | (2006.01) |
| *B29C 65/82* | (2006.01) |
| *B29C 65/00* | (2006.01) |
| *B29L 31/48* | (2006.01) |

(52) U.S. Cl.
CPC ............ *A61F 13/49* (2013.01); *B29C 65/086* (2013.01); *B29C 65/7891* (2013.01); *B29C 65/8253* (2013.01); *B29C 66/1122* (2013.01); *B29C 66/431* (2013.01); *B29C 66/73921* (2013.01); *B29C 66/8167* (2013.01); *B29C 66/81427* (2013.01); *B29C 66/81469* (2013.01); *B29C 66/83411* (2013.01); *B29C 66/92431* (2013.01); *B29C 66/92443* (2013.01); *B29C 66/92921* (2013.01); *B32B 37/06* (2013.01); *B32B 37/10* (2013.01); *B32B 37/20* (2013.01); *B29C 66/433* (2013.01); *B29C 66/7294* (2013.01); *B29L 2031/4878* (2013.01); *B32B 2555/02* (2013.01); *F04C 2270/0421* (2013.01); *Y10T 156/17* (2015.01)

(58) Field of Classification Search
CPC ........ B29C 66/73921; B29C 66/81427; B29C 66/81469; B29C 66/8167; B29C 66/83411; B29C 66/92431; B29C 66/92443; B29C 66/92921
USPC ........................................................ 156/73.1
See application file for complete search history.

(56) References Cited

U.S. PATENT DOCUMENTS

| | | | |
|---|---|---|---|
| 5,256,231 | A | 10/1993 | Gorman et al. |
| 5,354,591 | A | 10/1994 | Ott et al. |
| 5,464,401 | A | 11/1995 | Hasse et al. |
| 5,496,429 | A | 3/1996 | Hasse et al. |
| 5,611,791 | A | 3/1997 | Gorman et al. |
| 5,616,394 | A | 4/1997 | Gorman et al. |
| 5,643,397 | A | 7/1997 | Gorman et al. |
| 6,004,427 | A * | 12/1999 | Kohn .................... B29C 65/086 156/580.1 |
| 6,508,641 | B1 * | 1/2003 | Kubik .................. B29C 65/086 156/580.1 |
| 2003/0212377 | A1 | 11/2003 | Karlsson |
| 2004/0114662 | A1 | 6/2004 | Messler |
| 2004/0216830 | A1 * | 11/2004 | Van Eperen ...... A61F 13/15723 156/73.1 |
| 2008/0110550 | A1 * | 5/2008 | Lehto ................ B29C 66/92611 156/73.1 |
| 2009/0048572 | A1 | 2/2009 | Karlsson |
| 2010/0108268 | A1 | 5/2010 | Yamamoto et al. |

FOREIGN PATENT DOCUMENTS

| | | |
|---|---|---|
| JP | 5-15551 | 1/1993 |
| JP | 7-501245 | 2/1995 |
| JP | 9-57853 | 3/1997 |
| JP | 10-272697 | 10/1998 |
| JP | 2004-525382 | 8/2004 |
| JP | 2005-521475 | 7/2005 |
| JP | 2008-253633 | 10/2008 |

* cited by examiner

METHOD FOR PRODUCING DISPOSABLE WORN ARTICLE AND WELDING DEVICE USED IN SAME

TECHNICAL FIELD

The present invention relates to a method for producing a disposable worn article having welded portions in which mutually-facing thermoplastic sheets are welded to each other by ultrasonic waves and a welding device used in the same.

BACKGROUND ART

Conventionally, a disposable diaper having a front belly part, a back part, and a crotch part has been, for example, known as the worn article described above. In the disposable diaper, the front belly part and the back part are welded to each other by ultrasonic waves through a pair of side seal portions (welded portions).

As a method for forming the side seal portions, there has been employed a method for continuously supplying at least a pair of thermoplastic sheets for constituting the front belly part and the back part to the place between an anvil rotatable about a predetermined shaft and a horn arranged facing the peripheral surface of the anvil (for example, Japanese Unexamined Patent Publication No. H05-15551). The respective thermoplastic sheets are supplied to the place between the anvil and the horn in a state of facing each other.

On the peripheral surface of the anvil, protruding portions are intermittently formed in a circumferential direction. Therefore, the thermoplastic sheets continuously supplied to the place between the anvil and the horn are intermittently welded to each other by ultrasonic waves at a cycle at which the protruding portions come close to the horn. Thus, the mutually-facing thermoplastic sheets are welded to each other to form the welded portions.

According to the producing method described in Japanese Unexamined Patent Publication No. H05-15551, the welded portions are intermittently formed with respect to the continuously-supplied thermoplastic sheets (hereinafter referred to as a continuous supplying method). On the other hand, there has been known a method in which welded portions are continuously formed with respect to intermittently-supplied thermoplastic sheets (hereinafter referred to as an intermittent supplying method).

In order to perform the intermittent supplying method, it is assumed that the thermoplastic sheets are intermittently supplied to the place between an anvil in which the protruding portions are intermittently provided and a horn at a cycle at which the protruding portions come close to the horn in the same way as the continuous supplying method. In this case, however, the following problem arises.

As shown in FIG. 9, a welding force (referred to as a force in some cases) for welding the thermoplastic sheets to each other is generated between the anvil and the horn. The welding force becomes gradually greater and reaches its peak as the protruding portions of the anvil come close to the horn, and becomes smaller as the protruding portions separate from the horn. That is, a time lag is generated until the welding force is increased to a required welding force after the protruding portions of the anvil come close to the horn. Therefore, in the chevron waveform of the welding force, the welding force sufficiently contributes to the welding of the thermoplastic sheets only in a certain period (for example, a period T1 shown in FIG. 9).

Accordingly, in order to obtain sufficient energy (a hatched area in FIG. 9) for the welding, it is required to increase the peak value (power to obtain the value) of the welding force and decrease the supplying rate (the rotating rate of the anvil) of the thermoplastic sheets to increase the period T1.

SUMMARY OF THE INVENTION

It is an object of the present invention to provide a method for producing a disposable worn article and a welding device used in the same that are capable of increasing the supplying rate of thermoplastic sheets while reducing a welding force as an intermittent supplying method compared with a case in which an anvil and a horn come close to and separate from each other at a predetermined cycle.

The inventors of the present application have found out the point that a constant welding force is generated between an anvil and a horn arranged with a constant interval therebetween regardless of whether thermoplastic sheets are supplied. That is, although it has been conventionally recognized that a welding force is generated between the anvil and the horn based on the premise that thermoplastic sheets are interposed between the anvil and the horn, the welding force is actually generated between the anvil and the horn according to the interval between them even in a state in which the thermoplastic sheets are not interposed between the anvil and the horn.

In view of the point, the inventors of the present application have conceived the present invention that rotates an anvil while maintaining the interval between the anvil and horn at a constant interval.

Specifically, the present invention provides a method for producing a disposable worn article in which a welding target component having facing portions is continuously welded with a predetermined pattern in a range from one end portion to the other end portion of the facing portions, the facing portions being two mutually-facing portions constituted by thermoplastic sheets, the method comprising: a rotating step of rotating an anvil about a predetermined rotating shaft, the anvil having a welding surface for continuously welding the facing portions to each other with the predetermined pattern between the welding surface and a horn for applying ultrasonic vibrations to the facing portions; and a welding step of intermittently supplying, in a state in which the anvil is rotated, a plurality of the welding target components to place between the welding surface of the anvil and the horn to continuously weld the facing portions to each other with the predetermined pattern in each of the welding target components, wherein the welding surface of the anvil is provided over a whole circumference about the rotating shaft such that an interval between the welding surface of the anvil and the horn is maintained at an interval at which the facing portions are continuously weldable to each other with the predetermined pattern regardless of a rotating position of the anvil in the rotating step.

In addition, the present invention provides a welding device that continuously welds a welding target component having facing portions by ultrasonic waves with a predetermined pattern in a range from one end portion to the other end portion of the facing portions to produce a disposable worn article, the facing portions being two mutually-facing portions constituted by thermoplastic sheets, the welding device comprising: a horn for applying ultrasonic vibrations to the facing portions; an anvil that has a welding surface for continuously welding the facing portions to each other with the predetermined pattern between the welding surface and the horn and is rotatable about a predetermined rotating shaft; and a supplying mechanism that intermittently supplies, in a state in which the anvil is rotated, a plurality of the welding target components to a place between the welding surface of the anvil and the horn, wherein the welding surface of the anvil is provided over a whole circumference about the rotating shaft such that an interval between the welding surface of the anvil and the horn is maintained at an interval at which the facing portions are continuously weldable to each other with the predetermined pattern regardless of a rotating position of the anvil.

According to the present invention, it is possible to increase the supplying rate of thermoplastic sheets while reducing a welding force compared with a case in which an anvil and a horn come close to and separate from each other at a predetermined cycle.

DESCRIPTION OF EMBODIMENTS

Hereinafter, a description will be given of an embodiment of the present invention with reference to the accompanying drawings. Note that the following embodiment is a materialized example of the present invention but does not limit the technical scope of the present invention.

Figure 1:
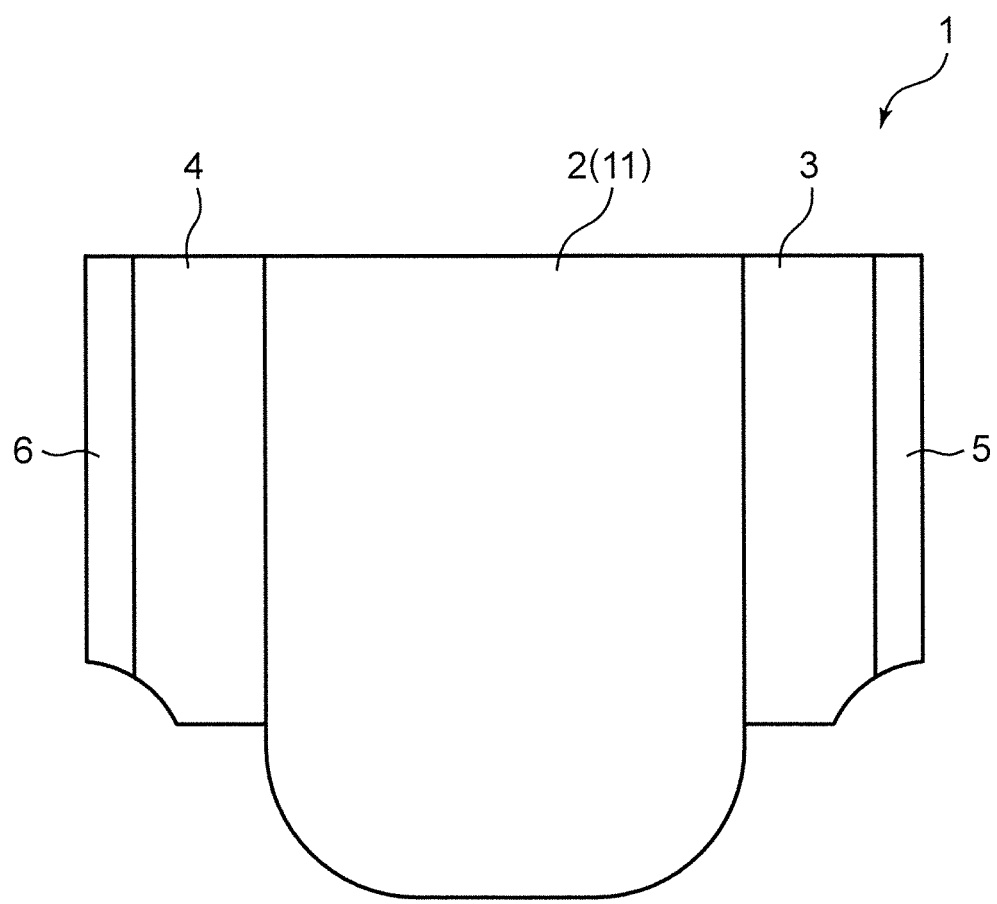
FIG. 1 is a front view showing a disposable diaper according to an embodiment of the present invention.
Figure 2:
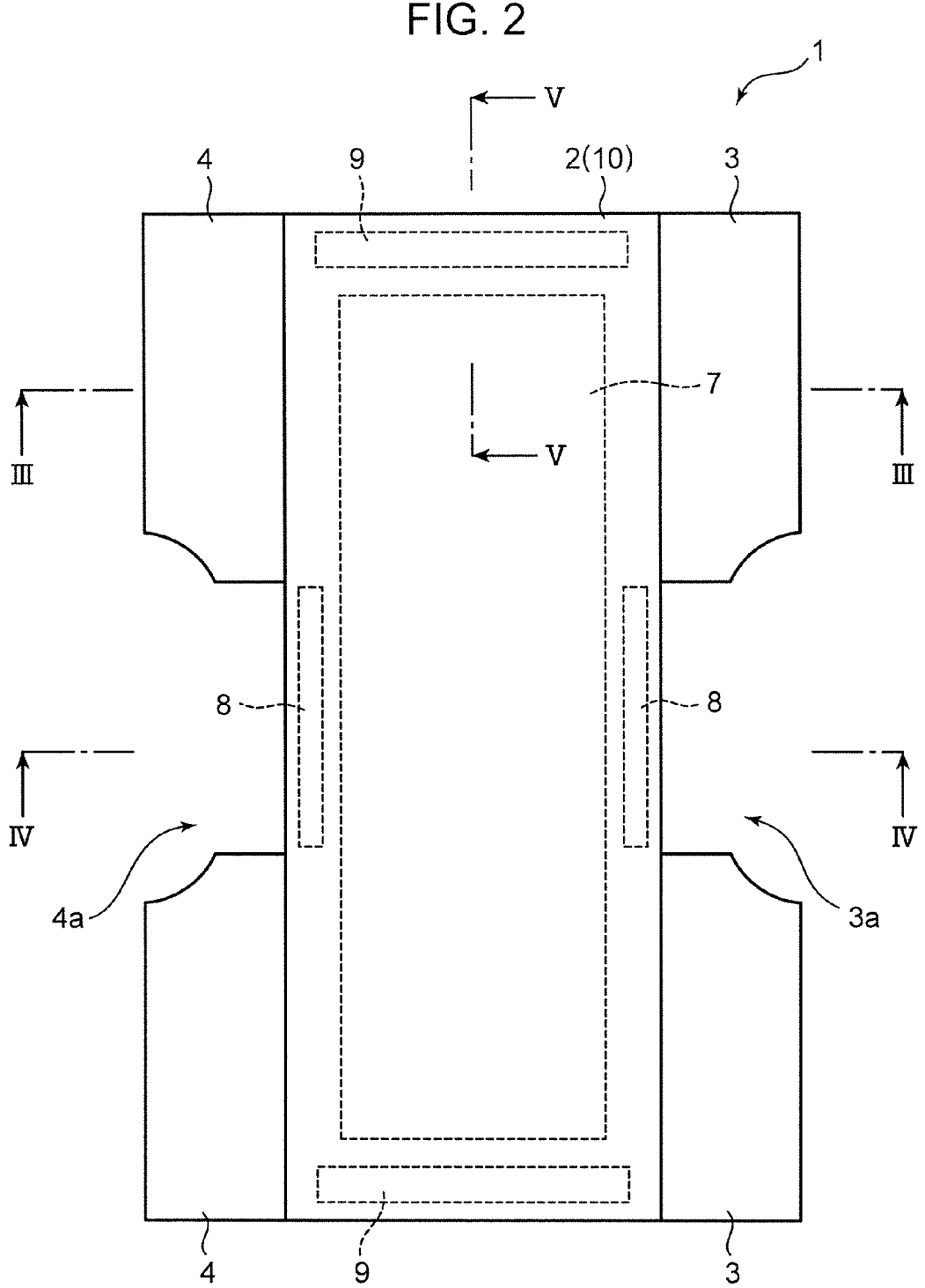
FIG. 2 is a plan view showing the disposable diaper shown in FIG. 1 in a state that the side seal portions are unfolded.

With reference to FIGS. 1 and 2, a disposable diaper 1 as an example of disposable worn articles is a so-called underpants-shaped diaper. Specifically, the disposable diaper 1 has a diaper main body 2 that extends from the front belly part to the back part via the crotch part of a wearer and four side panel pieces 3 and 4 that cover the side surfaces of the lumbar part of the wearer when the disposable diaper 1 is worn. The disposable diaper 1 is formed in an underpants shape when the respective side panel pieces 3 are bonded to each other through their side seal portions 5 and the respective side panel pieces 4 are bonded to each other through their side seal portions 6 in a state in which the diaper main body 2 is folded in half.

Hereinafter, a description will be given of the specific configuration of the disposable diaper 1 with reference to FIGS. 1 to 5.

The diaper main body 2 is capable of absorbing body wastes (for example, urine) of a wearer and has elasticity at its appropriate portions. Specifically, the diaper main body 2 has an absorber 7 capable of absorbing body wastes of a wearer, elastic members 8 for legs provided at positions corresponding to the crotch part of the wearer, a pair of elastic members 9 for waist provided at positions corresponding to the front belly part and the back part of the wearer, and inner and outer sheets 10 and 11 that sandwich the absorber 7, the elastic members 8 for legs, and the elastic members 9 for waist between them.

The inner sheet 10 is a substantially rectangular sheet that is directed to the body surface side of a wearer when the disposable diaper 1 is worn and has liquid permeability. The inner sheet 10 can be constituted by, for example, a nonwoven sheet and/or a mesh sheet having liquid permeability.

The outer sheet 11 is a sheet that is directed to the outer side of a wearer when the disposable diaper 1 is worn and has liquid impermeability. The outer sheet 11 can be constituted by a polyethylene film or a nonwoven fabric having water repellency and air permeability. In addition, the outer sheet 11 is a substantially rectangular sheet having a size equivalent to that of the inner sheet 10.

Figure 3:
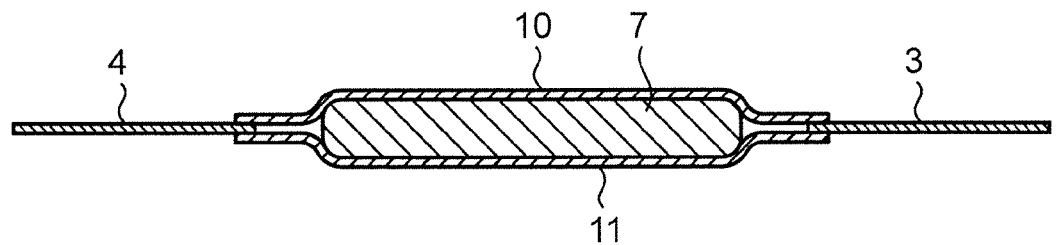
FIG. 3 is a cross-sectional view taken along line III-III in FIG. 2.

The absorber 7 absorbs liquid that passes through the inner sheet 10. Specifically, the absorber 7 is molded in such a way as to stack crashed pulps or materials in which crashed pulps and highly water-absorptive polymers are mixed together. In addition, the absorber 7 has a substantially rectangular shape or a hourglass shape having a longitudinal size smaller than those of the respective sheets 10 and 11 and a width size narrower than those of the respective sheets 10 and 11. The absorber 7 is arranged between the sheets 10 and 11 such that vacant areas exist at both end portions in the longitudinal direction of the respective sheets 10 and 11 and at both end portions in the width direction (horizontal direction) of the respective sheets 10 and 11. Further, as shown in FIG. 3, the absorber 7 is bonded to the sheets 10 and 11 in a state of being sandwiched between the inner sheet 10 and the outer sheet 11.

Figure 4:
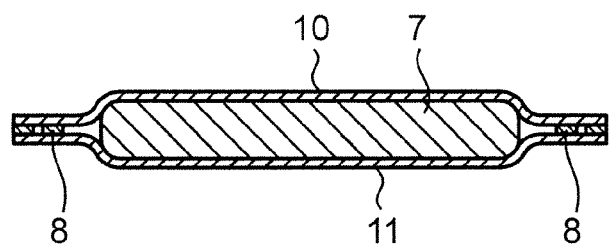
FIG. 4 is a cross-sectional view taken along line IV-IV in FIG. 2.

The respective elastic members 8 for legs are such that the diaper main body 2 is raised and brought into intimate contact with the crotch part of a wearer when the disposable diaper 1 is worn to prevent body wastes from leaking from the gap between the diaper main body 2 and the body surface of the wearer. At least parts of the respective elastic members 8 for legs are provided at positions on both outer sides in the width direction of the absorber 7 and at positions between the respective side panel pieces 3 and between the respective side panel pieces 4. In addition, the respective elastic members 8 for legs are attached on the diaper main body 2 in their expanding state in the longitudinal direction of the diaper main body 2. As shown in FIG. 4, the respective elastic members 8 for legs are bonded to the sheets 10 and 11 in a state of being sandwiched between the inner sheet 10 and the outer sheet 11. The respective elastic members 8 for legs can be constituted by polyurethane, natural rubber, or sheets or threads made of a thermoplastic resin.

Figure 5:
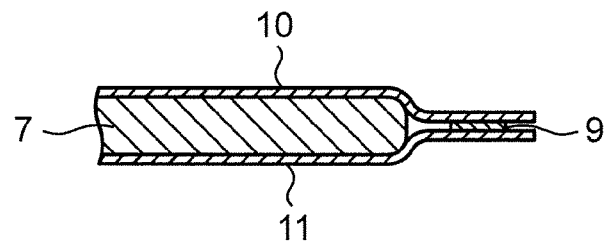
FIG. 5 is a cross-sectional view taken along line V-V in FIG. 2.

The respective elastic members 9 for waist are such that the diaper main body 2 is fastened to the front belly part or the back part of a wearer when the disposable diaper 1 is worn to prevent the disposable diaper 1 from being pulled down. The respective elastic members 9 for waist are attached on the diaper main body 2 under a stretched state in the width direction of the absorber 7. As shown in FIG. 5, the respective elastic members 9 for waist are bonded to the sheets 10 and 11 in a state of being sandwiched between the inner sheet 10 and the outer sheet 11. The respective elastic members 9 for waist can be constituted by polyurethane, natural rubber, or sheets or threads made of a thermoplastic resin.

The respective side panel pieces 3 extend from both end portions in the longitudinal direction (front and rear direction) of the diaper main body 2 to one side in the horizontal direction (right side in FIGS. 1 and 2) and has elasticity in the horizontal direction. A gap portion 3a is formed between the respective side panel pieces 3 and used as a leg hole when the right edge portions of the respective side panel pieces 3 are bonded to each other through the side seal portions 5. As shown in FIG. 3, the respective side panel pieces 3 are bonded to the sheets 10 and 11 in a state of being sandwiched between the inner sheet 10 and the outer sheet 11 on the right side of the absorber 7.

In addition, the respective side panel pieces 3 are sheets made of a thermoplastic material. Specifically, the respective side panel pieces 3 can be constituted by an elastic film, an elastic nonwoven fabric, a laminated body of an elastic film and a nonwoven fabric, or a laminated body of thread rubber and a nonwoven fabric each of which is made of one or at least two of the materials of a block copolymer of polystyrene, a block copolymer of polyisoprene, a block copolymer of polybutadiene, a copolymer of ethylene, natural rubber, and urethane.

The respective side panel pieces 4 extend from both end portions in the longitudinal direction of the diaper main body 2 to one side in the horizontal direction (left side in FIGS. 1 and 2) and has elasticity in the horizontal direction. A gap portion 4a is formed between the respective side panel pieces 4 and used as a leg hole when the left edge portions of the respective side panel pieces 4 are bonded to each other through the side seal portions 6. As shown in FIG. 3, the respective side panel pieces 4 are bonded to the sheets 10 and 11 in a state of being sandwiched between the inner sheet 10 and the outer sheet 11 on the left side of the absorber 7.

In addition, the respective side panel pieces 4 are sheets made of a thermoplastic material. Specifically, the respective side panel pieces 4 can be constituted by an elastic film, an elastic nonwoven fabric, a laminated body of an elastic film and a nonwoven fabric, or a laminated body of thread rubber and a nonwoven fabric each of which is made of one or at least two of the materials of a block copolymer of polystyrene, a block copolymer of polyisoprene, a block copolymer of polybutadiene, a copolymer of ethylene, natural rubber, and urethane.

Hereinafter, a description will be given of a method of producing the disposable diaper 1 with reference to FIG. 6. The method of producing the disposable diaper 1 mainly includes the following steps S1 to S12.

<Step S1>

In step S1, an outer sheet band 11A for constituting the outer sheet 11 is continuously conveyed in its longitudinal direction.

<Step S2>

In step S2, the elastic members 9 for waist are bonded to the continuously-conveyed outer sheet band 11A. Specifically, the elastic members 9 for waist are arranged at two parts on the outer sheet band 11A with an interval corresponding to the longitudinal size of the absorber 7. In addition, the elastic members 9 for waist at the two parts attached in step S2 are separated from each other in the longitudinal direction (flow direction) of the outer sheet band 11A. Moreover, the respective elastic members 9 for waist are attached on the outer sheet band 11A under a stretched state in the width direction of the outer sheet band 11A.

<Step S3>

In step S3, the absorber 7 is bonded to the continuously-conveyed outer sheet band 11A. Specifically, the absorber 7 is arranged between the respective elastic members 9 for waist with its longitudinal direction parallel to the longitudinal direction of the outer sheet band 11A.

<Step S4>

In step S4, the pair of elastic members 8 for legs is bonded to the continuously-conveyed outer sheet band 11A. The elastic members 8 for legs are arranged at a central position in the longitudinal direction of the absorber 7 on the outer sheet band 11A and at positions on both outer sides in the width direction of the absorber 7. In addition, the respective elastic members 8 for legs are attached on the outer sheet band 11A under a stretched state in the longitudinal direction of the outer sheet band 11A.

<Step S5>

In step S5, a side panel band 3A for constituting the side panel pieces 3 and a side panel band 4A for constituting the side panel pieces 4 are bonded to the continuously-conveyed outer sheet band 11A. The side panel bands 3A and 4A are continuously supplied with their longitudinal direction parallel to the longitudinal direction of the outer sheet band 11A and bonded to the edge portions of the outer sheet band 11A on the outer sides of the elastic members 8 for legs. At this time, the side panel bands 3A and 4A are bonded to the outer sheet band 11A in a state of protruding from the outer sheet band 11A.

<Step S6>

In step S6, an inner sheet band 10A for constituting the inner sheet 10 is bonded to the continuously-conveyed outer sheet band 11A. Specifically, the inner sheet band 10A is continuously supplied with its longitudinal direction parallel to the longitudinal direction of the outer sheet band 11A and bonded to the outer sheet band 11A with its width direction aligned with the width direction of the outer sheet band 11A. In step S6, the respective elastic members 8 and 9 and the absorber 7 are entirely sandwiched between the sheet bands 10A and 11A, and the edge portions of the side panel bands 3A and 4A are sandwiched between the sheet bands 10A and 11A.

<Step S7>

In step S7, the side panel bands 3A and 4A are cut off to form the gap portions 3a and 4a. At this time, the side panel bands 3A and 4A are cut off over a predetermined range in the longitudinal direction of the respective side panel bands 3A and 4A, including the central position in the longitudinal direction of the absorber 7.

<Step S8>

In step S8, the sheet bands 10A and 11A and the side panel bands 3A and 4A are cut off to form a partly-finished product (welding target component) 1Z of a disposable diaper. Specifically, the sheet bands 10A and 11A and the side panel bands 3A and 4A are cut off at their positions between the adjacent elastic members 9 for waist. In step S8, the partly-finished product 1Z is formed in which the side panel bands 3A and 4A are separated into the side panel pieces 3 and 4, respectively.

<Step S9>

In step S9, for the diaper main body 2, the partly-finished product 1Z is folded in half at the central position in the longitudinal direction. Thus, the side panel pieces 3 face each other, and the side panel pieces 4 face each other (facing portions are formed by the two thermoplastic sheets).

<Step S10>

In step S10, the side seal portions 5 are formed on the respective side panel pieces 3, and the side seal portions 6 are formed on the respective side panel pieces 4. That is, the respective side panel pieces 3 and 4 are welded to each other by ultrasonic welding. Information on step S10 will be described in detail later.

<Step S11>

In step S11, the separated portion 3b on the outer side of the respective side seal portions 5 of the respective side panel pieces 3 is cut off, and the separated portion 4b on the outer side of the respective side seal portions 6 of the respective side panel pieces 4 is cut off. Thus, the edge portions of the respective side panel pieces 3 and the edge portions of the respective side panel pieces 4 are lined up to enhance the appearance.

<Step S12>

In step S12, the respective side panel pieces 3 and 4 are folded toward the inner side of the diaper main body 2. Thus, the disposable diaper 1 in a form suitable to be packaged is completed.

Next, a description will be given, with reference to FIGS. 7 and 8, of a welding device 14 used in step S10.

The welding device 14 has an anvil 16 that is rotatable about a rotating shaft J1, a pair of ultrasonic welding machines 17 (only one shown in FIG. 7) that welds the respective side panel pieces 3 and 4 to each other between the ultrasonic welding machines 17 and the anvil 16 by ultrasonic wave, a welding machine mounting section 18 on which the respective ultrasonic welding machines 17 are mounted, a conveyor (supplying mechanism) 15 that conveys the partly-finished product 1Z (see FIG. 6) of a diaper along a path R1 that passes through the places between the anvil 16 and the respective ultrasonic welding machines 17, and an image pick-up unit 27 that picks up an image of welded portions.

The anvil 16 has an anvil main body 16a and a pair of protruding portions 16b that protrudes from the anvil main body 16a to an outside. The respective protruding portions 16b are arranged at an interval corresponding to the pitch between the side seal portions 5 and 6. In addition, the respective protruding portions 16b are formed over the whole circumference of the anvil main body 16a. The peripheral surfaces of the respective protruding portions 16b constitute welding surfaces for continuously welding the respective side panel pieces 3 and 4 to each other with a predetermined pattern between the peripheral surfaces and horns 25 that will be described later. In addition, the peripheral surfaces of the respective protruding portions 16b are constituted by a column surface positioned about the rotating shaft J1 in order to weld the respective side panel pieces 3 and 4 to each other at the entire welding ranges thereof with uniform strength.

The respective ultrasonic welding machines 17 have a similar configuration. Therefore, only one of the configurations of the respective ultrasonic welding machines 17 will be described, while the other thereof will be omitted. The ultrasonic welding machine 17 has a transmitter (not shown) that generates mechanical vibrations according to the supply of power, the horns 25 for transmitting the vibrations from the transmitter to the respective side panel pieces 3 and 4, and a holding member 24 for holding the horns 25. oscillating surfaces 25a of the horns 25 are arranged facing the peripheral surfaces of the respective protruding portions 16b of the anvil 16 and extend in a tangential direction D1 (see FIG. 7) to the peripheral surfaces of the respective protruding portions 16b.

In addition, the ultrasonic welding machine 17 is mounted on the welding machine mounting section 18 so as to allow the adjustment of its mounting position in the tangential direction D1. Specifically, the welding machine mounting section 18 has a bracket 18a to which the holding member 24 is fixed and a frame 18b on which the bracket 18a is mounted. The bracket 18a has three long holes 18c that extend along the tangential direction D1. When bolts 26 inserted in the respective long holes 18c are threadedly engaged with the female screw portions (not shown) of the frame 18b, the bracket 18a can be mounted on the frame 18b. On the other hand, when the bolts 26 are loosed to move inside the long holes 18c, the mounting position of the ultrasonic welding machine 17 (the bracket 18a) can be adjusted in the tangential direction D1.

The conveyor 15 is capable of supplying the welded portions (facing portions) of the respective side panel pieces 3 and 4 to the places between the peripheral surfaces of the anvil 16 and the horns 25 in a state in which the partly-finished product 1Z of a diaper is sandwiched from both front and rear sides thereof on both sides of the respective horns 25. That is, the conveyor 15 conveys the partly-finished product 1Z in a state in which portions other than the welded portions of the partly-finished product 1Z are sandwiched.

Specifically, the conveyor 15 has an inner support belt 19 that supports the partly-finished product 1Z from the side of the anvil 16 on the inner side of the respective horns 25, a pair of outer support belts 20 that supports the partly-finished product 1Z from the side of the anvil 16 on the outer sides of the respective horns 25, a main body sandwiching belt 21 that sandwiches the diaper main body 2 between the main body sandwiching belt 21 and the inner support belt 19, a pair of panel sandwiching belts 22 that sandwiches the side panel pieces 3 and 4 between the panel sandwiching belts 22 and the inner support belt 19, and a pair of separated portion sandwiching belts 23 that sandwiches portions corresponding to the separated portions 3b and 4b (see FIG. 6) of the side panel pieces 3 and 4 between the separated portion sandwiching belt 23 and the respective outer support belts 20. The conveyor 15 is bridged between a driving roller and a plurality of rolling rollers (each not shown) and circulates along predetermined paths including the path R1 according to the driving of the driving roller.

Figure 7:
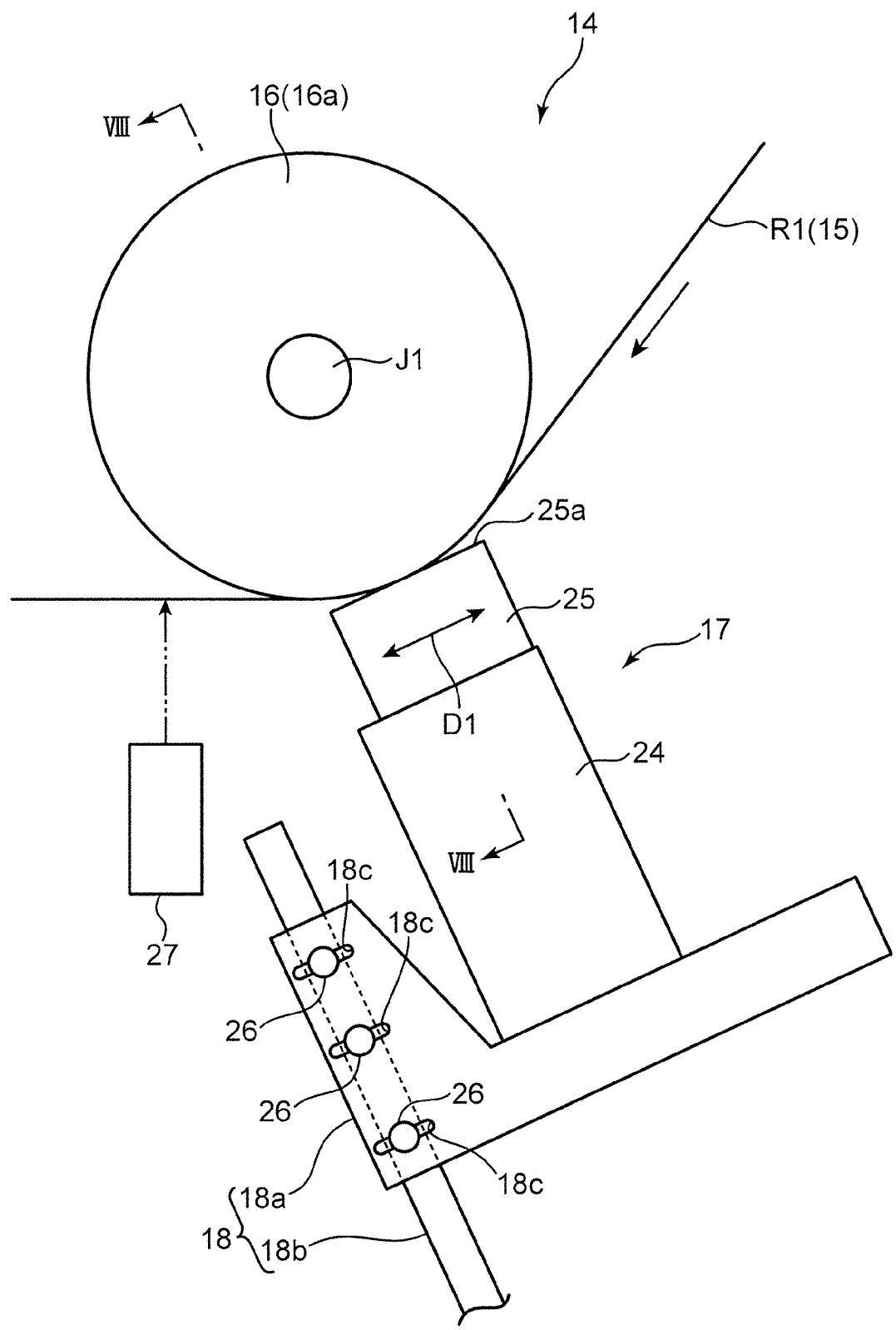
FIG. 7 is a schematic view showing the entire configuration of the welding device for performing a welding step in FIG. 6.
Figure 8:
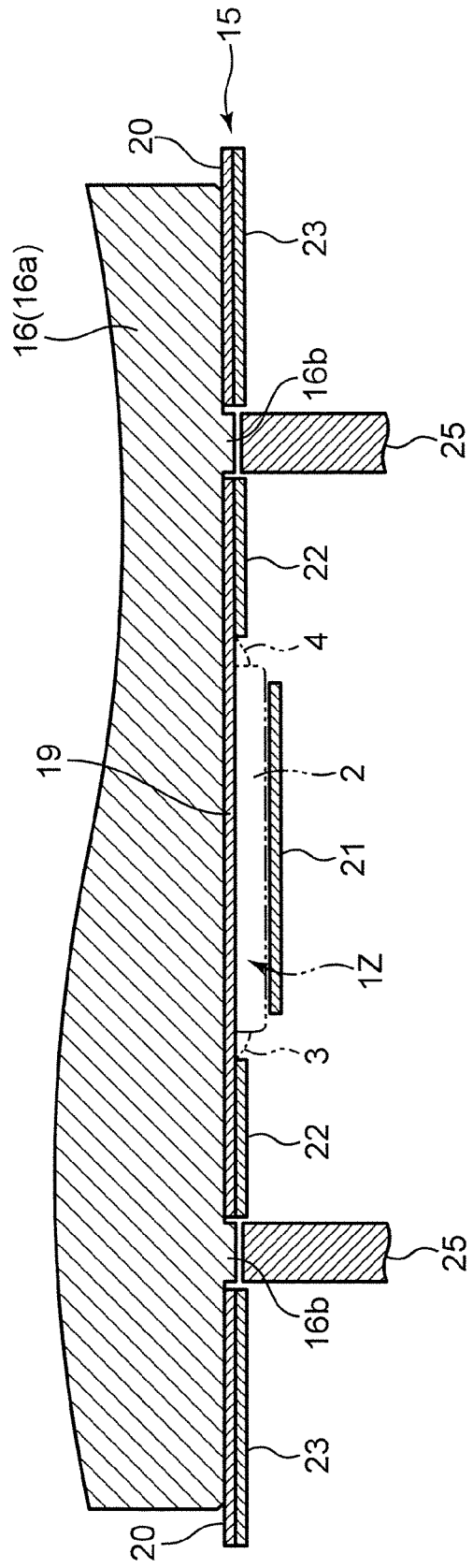
FIG. 8 is a cross-sectional view taken along line VIII-VIII in FIG. 7.

The image pick-up unit 27 is arranged on the downstream side of the anvil 16 and the ultrasonic welding machines 17 as shown in FIG. 7 and picks up an image of the welded portions (the side seal portions 5 and 6) of the side panel pieces 3 and 4 in a state in which the partly-finished product 1Z is sandwiched by the conveyor 15.

Hereinafter, a description will be given of the operation of the welding device 14.

The welding device 14 rotates the anvil 16 about the rotating shaft J1 (rotating step). Here, the welding device 14 may rotate the anvil 16 using the power of a driving unit (for example, a motor) (not shown) but is also allowed to rotate the same in response to (in conjunction with) the operation of the conveyor 15.

Figure 10:
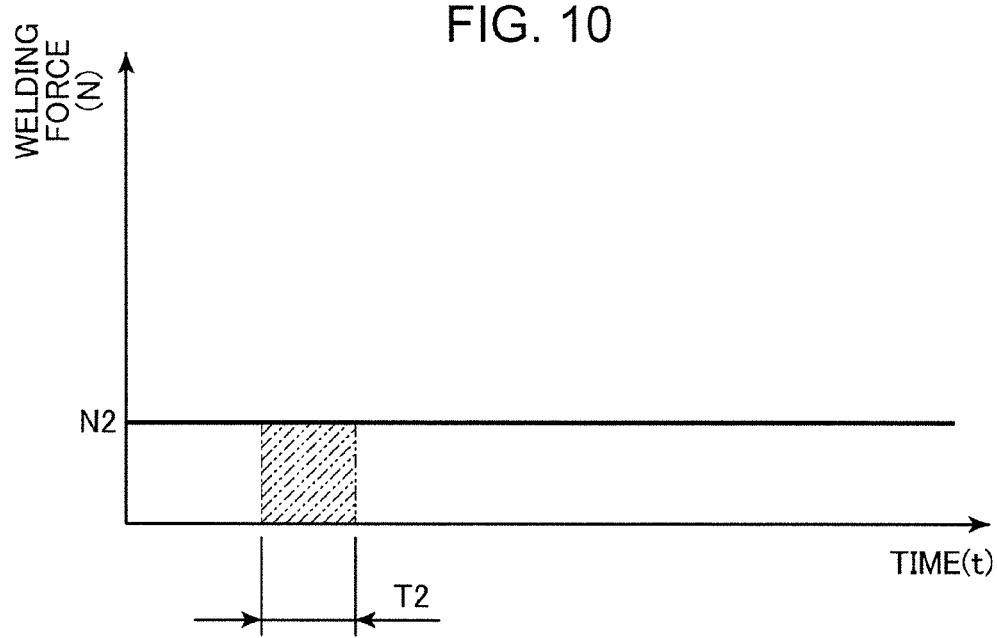
FIG. 10 is a graph for describing a welding force in the welding device shown in FIG. 7.

Here, the peripheral surfaces of the protruding portions 16b of the anvil 16 are provided over the whole circumference about the rotating shaft J1 such that the interval between the peripheral surfaces of the protruding portions 16b and the horns 25 is maintained at an interval at which the respective side panel pieces 3 and 4 may be continuously welded to each other with a predetermined pattern regardless of the rotating position of the anvil 16. Therefore, as shown in FIG. 10, a constant welding force N2 is generated between the peripheral surfaces of (the protruding portions 16b of) the anvil 16 and (the oscillating surfaces 25a of) the horns 25 in the rotating step regardless of whether the partly-finished product 1Z is supplied.

Then, the welding device 14 drives, in a state in which the anvil 16 is rotated, the conveyor 15 to intermittently supply the plurality of partly-finished products 1Z to the place between the anvil 16 and the horns 25. Thus, the respective side panel pieces 3 and 4 in each of the partly-finished products 1Z are continuously welded to each other by the welding force N2 to form the side seal portions 5 and 6 (see FIG. 1) (welding step).

In the welding step, the partly-finished products 1Z are sandwiched by the conveyor 15. Therefore, the partly-finished products 1Z can be prevented from being displaced from the anvil 16 and the ultrasonic welding machines 17.

Next, the welding device 14 picks up an image of the side seal portions 5 and 6 of the side panel pieces 3 and 4 with the image pick-up unit 27 in a state in which the partly-finished product 1Z is sandwiched by the conveyor 15 (image pick-up step). The image pick-up step is performed in a state in which the partly-finished product 1Z is sandwiched by the conveyor 15. Therefore, a problem in which the side panel pieces 3 and 4 unexpectedly appear in an image pick-up range or the like can be prevented. Then, image pick-up data obtained in the image pick-up step is used in, for example, determination as to whether the side seal portions 5 and 6 have been properly formed.

Then, when parts of the oscillating surfaces 25a of the horns 25 facing the anvil 16 are degraded after the welding of the side panel pieces 3 and 4 as described above, an adjustment step is performed. In the adjustment step, nuts 28 are loosed to move the bolts 26 inside the long holes 18c of the welding machine mounting section 18 such that portions other than the degraded portions of the oscillating surfaces 25a face the anvil 16. When the nuts 28 are fastened again in this state, the ultrasonic welding machines 17 are fixed to the welding machine mounting section 18. Thus, the mounting positions of the ultrasonic welding machines 17 can be moved in the tangential direction D1.

As described above, the peripheral surfaces (welding surfaces) of the protruding portions 16b of the anvil 16 are provided over the whole circumference about the rotating shaft J1 such that the interval between the welding surfaces of the anvil 16 and the horns 25 is maintained at the interval at which the respective side panel pieces 3 and 4 may be continuously welded to each other with a predetermined pattern regardless of the rotating position of the anvil 16. Therefore, as shown in FIG. 10, the constant welding force N2 can be generated regardless of whether the partly-finished product 1Z is supplied.

Figure 9:
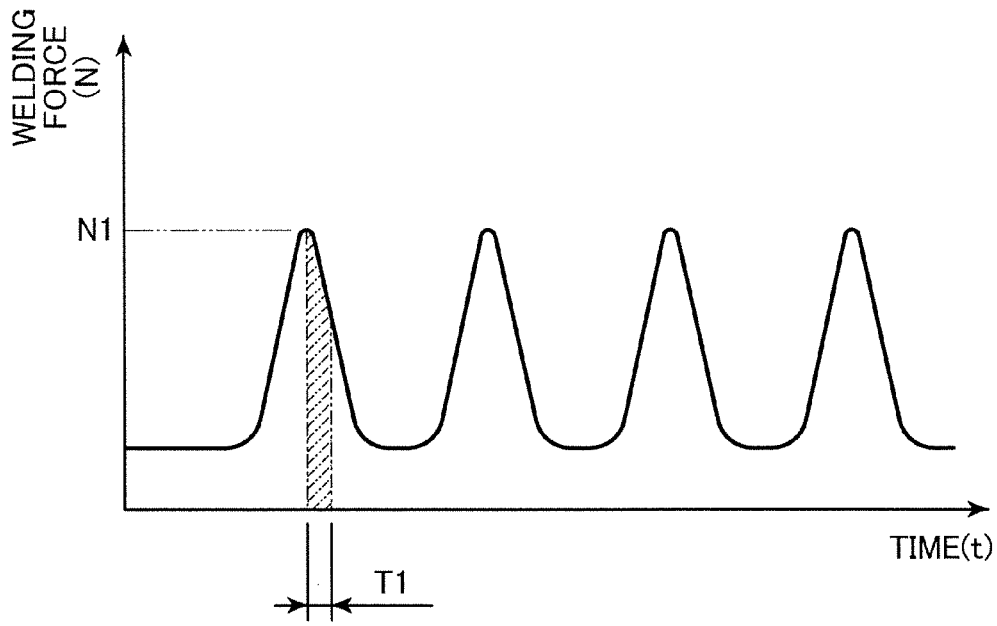
FIG. 9 is a graph for describing a welding force in a conventional welding device.

Therefore, unlike a conventional case shown in FIG. 9, a time lag until the generation of the welding force can be prevented. Thus, the welding force N2 can be constantly used for the welding during a time T2 in which the partly-finished product 1Z passes through the place between the anvil 16 and the horns 25. Therefore, substantial energy (a hatched area in FIG. 10) for the welding can be obtained without decreasing the supplying rate of the partly-finished product 1Z. In addition, the time T2 in which the welding force is used can be increased as described above. Therefore, the welding force N2 (for example, 500 N to 600 N) for obtaining energy equivalent to energy (a hatched area in FIG. 9) for conventional welding can be made smaller than the peak value N1 (2000 N) of a conventional welding force.

Accordingly, it is possible to increase the supplying rate of the partly-finished product 1Z while reducing the welding force compared with the conventional case.

Further, the following effects can be obtained according to the embodiment.

When the interval between the peripheral surfaces of the anvil 16 and the horns 25 is maintained at a minute interval even in a state in which the partly-finished product 1Z is not supplied as described above, the degradation of the horns 25 is accelerated compared with a conventional case in which the interval is changed. To this end, in the embodiment, the positional relationship between the horns 25 and the anvil 16 is adjusted when parts of the oscillating surfaces 25a of the horns 25 are degraded. Thus, the ultrasonic welding can be continued using portions other than the degraded portions of the oscillating surfaces 25a. Accordingly, a time in which the welding operation is interrupted can be shortened compared with a case in which the horns 25 are replaced.

In addition, both sides of the welded portions of the partly-finished product 1Z are held by the plurality of belts 19 to 23. Thus, the welding target component can be prevented from expanding/contracting or moving in a direction orthogonal to the supplying direction of the partly-finished product 1Z. Therefore, the welding positions can be accurately held in the direction orthogonal to the supplying direction. Particularly, in the embodiment, the elastic members 9 for waist are attached on the partly-finished product 1Z under the stretched state in the direction orthogonal to the supplying direction. Therefore, the side panel pieces 3 and 4 can be effectively prevented from shrinking by the elastic forces.

Moreover, the image pick-up unit 27 picks up an image of the welded portions in a state in which the partly-finished product 1Z is sandwiched by the respective belts 19 to 23. Thus, both sides of the side seal portions 5 and 6 can be reliably prevented from unexpectedly appearing in an image pick-up range. Therefore, determination or the like using the result of picking up an image of the welded portions can be accurately performed.

Figure 11:
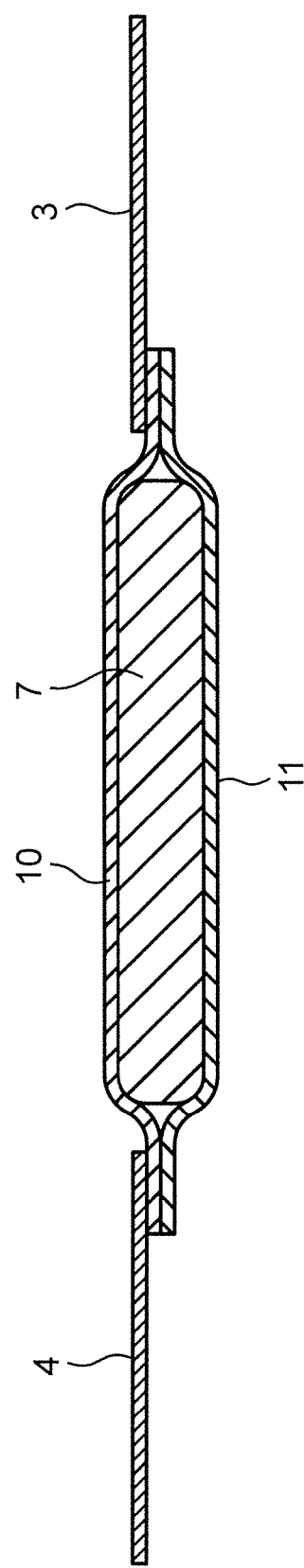
FIG. 11 is a view corresponding to FIG. 3, showing another embodiment of a disposable diaper.

Note that although the embodiment describes the disposable diaper 1 in which the side panel pieces 3 and 4 are sandwiched between the inner sheet 10 and the outer sheet 11 as shown in FIG. 3, the disposable diaper 1 can also have a configuration in which the respective side panel pieces 3 and 4 are bonded on the inner sheet 10 as shown in FIG. 11. In this case, it is necessary to reverse the order of steps S5 and S6 shown in FIG. 6.

In addition, although the embodiment describes the welding pattern in which the entire welding ranges of the side panel pieces 3 and 4 are welded with uniform strength, it may also employ a welding pattern in which the welding strength in the welding ranges is partially changed. Specifically, it may also employ a pattern in which the welded portions and the non-welded portions are alternately arranged side by side and employ a pattern in which the welded portions or the non-welded portions are arranged so as to be dotted. In this case, since the outer surfaces (welding surfaces) of the protruding portions 16b of the anvil 16 are required to have a concavo-convex shape corresponding to the welding pattern at the whole circumferences thereof, the welding force N2 in FIG. 10 is accompanied with pulsations. However, there is no doubt that the constant welding force is obtained regardless of whether the partly-finished product 1Z is supplied.

Figure 6:
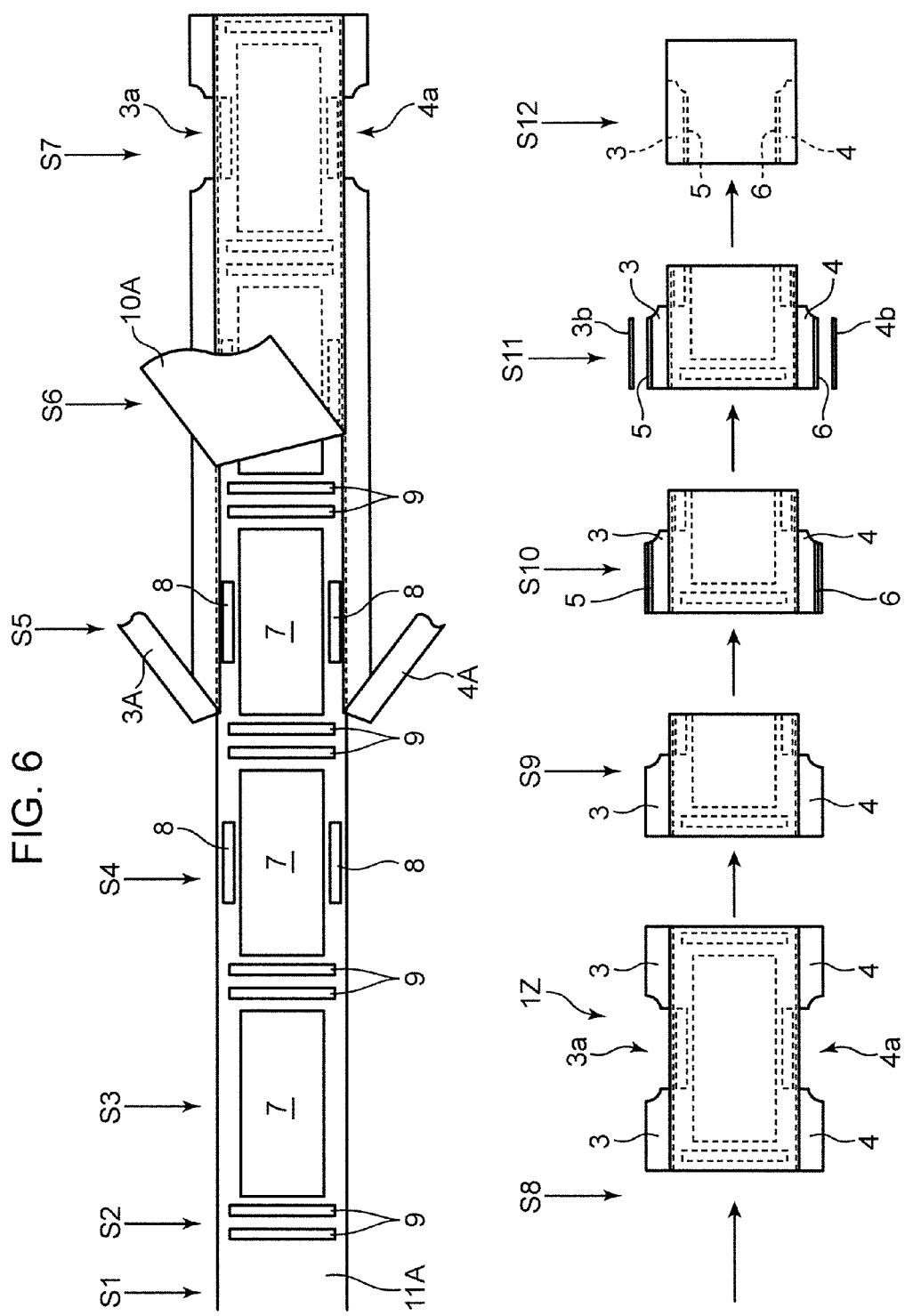
FIG. 6 is a process drawing showing a production method for the disposable diaper in FIG. 1.

Moreover, although the embodiment exemplifies the method in which the side panel bands 3A and 4A are bonded to the outer sheet band 11A in step S5 and cut off in step S7 as shown in FIG. 6, the method of forming the side panel pieces 3 and 4 is not limited to this. For example, the side panel pieces 3 and 4 may be prepared in advance and bonded to the outer sheet band 11A at a pitch corresponding to the gap portions 3a and 4a in step S5. In this case, step S7 may be omitted.

Further, the respective elastic members 8 for legs and the respective elastic members 9 for waist may be bonded to the inner side of the inner sheet 10 and/or the outer side of the outer sheet 11.

Furthermore, although the embodiment exemplifies the disposable diaper 1 as a disposable worn article, the welding method and the welding device 14 may also be used for sanitary napkins that hold an absorber between a pair of thermoplastic sheets, nonwoven gowns (operating gowns), or the like.

Note that the specific embodiment described above mainly includes the inventions having the following configurations.

The inventors of the present application have found out the point that a constant welding force is generated between an anvil and a horns arranged with a constant interval therebetween regardless of whether thermoplastic sheets are supplied. That is, although it has been conventionally recognized that a welding force is generated between the anvil and the horns based on the premise that thermoplastic sheets are interposed between the anvil and the horn, the welding force is actually generated between the anvil and the horn according to the interval between them even in a state in which the thermoplastic sheets are not interposed between the anvil and the horn.

Then, in view of the point, the inventors of the present application have conceived the present invention that rotates an anvil while maintaining the interval between the anvil and horn at a constant interval.

Specifically, the present invention provides a method for producing a disposable worn article in which a welding target component having facing portions is continuously welded with a predetermined pattern in a range from one end portion to the other end portion of the facing portions, the facing portions being two mutually-facing portions constituted by thermoplastic sheets, the method comprising: a rotating step of rotating an anvil about a predetermined rotating shaft, the anvil having welding surfaces for continuously welding the facing portions to each other with the predetermined pattern between the welding surfaces and a horn for applying ultrasonic vibrations to the facing portions; and a welding step of intermittently supplying, in a state in which the anvil is rotated, a plurality of the welding target components to places between the welding surfaces of the anvil and the horn to continuously weld the facing portions to each other with the predetermined pattern in each of the welding target components, wherein the welding surfaces of the anvil are provided over a whole circumference about the rotating shaft such that an interval between the welding surfaces of the anvil and the horn is maintained at an interval at which the facing portions are continuously weldable to each other with the predetermined pattern regardless of a rotating position of the anvil in the rotating step.

In addition, the present invention provides a welding device that continuously welds a welding target component having facing portions by ultrasonic waves with a predetermined pattern in a range from one end portion to the other end portion of the facing portions to produce a disposable worn article, the facing portions being two mutually-facing portions constituted by thermoplastic sheets, the welding device comprising: a horn for applying ultrasonic vibrations to the facing portions; an anvil that has welding surfaces for continuously welding the facing portions to each other with the predetermined pattern between the welding surfaces and the horn and is rotatable about a predetermined rotating shaft; and a supplying mechanism that intermittently supplies, in a state in which the anvil is rotated, a plurality of the welding target components to places between the welding surfaces of the anvil and the horn, wherein the welding surfaces of the anvil are provided over a whole circumference about the rotating shaft such that an interval between the welding surfaces of the anvil and the horn is maintained at an interval at which the facing portions are continuously weldable to each other with the predetermined pattern regardless of a rotating position of the anvil.

According to the present invention, the welding surface of the anvil is provided over the whole circumference about the rotating shaft such that the interval between the welding surface of the anvil and the horn is maintained at the interval at which the facing portions are continuously weldable to each other with the predetermined pattern regardless of the rotating position of the anvil. Therefore, as shown in FIG. 10, the constant welding force N2 can be generated regardless of whether the welding target component is supplied.

Therefore, unlike a conventional case shown in FIG. 9, a time lag until the generation of the welding force can be prevented. Thus, the welding force N2 can be constantly used for the welding during a time T2 in which the welding target component passes through the place between the anvil and the horn. Therefore, substantial energy (a hatched area in FIG. 10) for the welding can be obtained without reducing the supplying rate of the welding target component. In addition, the time T2 in which the welding force is used can be increased as described above. Therefore, the welding force N2 for obtaining energy equivalent to energy (a hatched area in FIG. 9) for conventional welding can be made smaller than the peak value N1 of a conventional welding force.

Thus, according to the present invention, it is possible to increase the supplying rate of the thermoplastic sheet while reducing the welding force compared with the conventional case.

Note that the "interval" between the welding surface of the anvil and the horn in the present invention refers to an interval in a part in which the welding surface of the anvil and (the oscillating surfaces of) the horn come closest to each other.

In addition, the "predetermined pattern" refers not only to a welding pattern with which the entirefacing portions are welded to each other by uniform welding strength but to a welding pattern with which the welding strength in the facing portions is partially changed. Specifically, the predetermined pattern includes a pattern in which the welded portions and the non-welded portions are alternately arranged side by side and a pattern in which the welded portions or the non-welded portions are arranged so as to be dotted. In this case, since the welding surface of the anvil are required to have a concavo-convex shape corresponding to the welding pattern over the whole circumferences thereof, the welding force N2 in FIG. 10 is accompanied with pulsations. However, there is no doubt that the constant welding force is obtained regardless of whether the welding target component is supplied. Then, the welding strength in the welded portions can be adjusted with such a pattern.

Moreover, the "two portions constituted by the thermoplastic sheets" refer not only to a case in which the two portions are each constituted by one thermoplastic sheet but to a case in which the two portions are each constituted by a plurality of thermoplastic sheets. Further, "continuously welding the facing portions to each other with the predetermined pattern" refers not only to a case in which only the facing portions are welded to each other but to a case in which the facing portions and the other thermoplastic members are simultaneously welded to each other.

Here, when the interval between the welding surface of the anvil and the horn is maintained at a minute interval even in a state in which the welding target component is not supplied as described above, the degradation of the horn is accelerated compared with a conventional case in which the interval is changed.

Therefore, in the method, the horns preferably has an oscillating surface that applies ultrasonic vibrations to the facing portions and extends in a tangential direction to the welding surface of the anvil, and the method for producing the worn article preferably further comprises an adjustment step of adjusting, when a portion of the oscillating surface facing the welding surface of the anvil is degraded, a positional relationship between the horn and the anvil such that a portion other than the degraded portion of the oscillating surface face the anvil.

In addition, the welding device preferably further comprises a mounting section on which the horn is mounted, wherein the horn preferably has an oscillating surface that applies ultrasonic vibrations to the facing portions and extends in a tangential direction to the welding surface of the anvil, and a mounting position of the horn with respect to the mounting section is preferably adjustable in the tangential direction.

According to these aspects, the positional relationship between the horn and the anvil is adjusted when a portion of the oscillating surface of the horn is degraded. Thus, the ultrasonic welding can be continued using a portion other than the degraded portion of the oscillating surface. Accordingly, a time in which the welding operation is interrupted can be shortened and it is cost-effective compared with a case in which the horn is replaced.

In the method, the welding step preferably supplies the facing portions to the place between the welding surface of the anvil and the horn in a state in which the welding target component is sandwiched from both front and rear sides thereof by a plurality of belts on both sides of the welded portion.

In addition, in the welding device, the supplying mechanism preferably has a plurality of belts capable of supplying the facing portions to the place between the welding surface of the anvil and the horn in a state in which the welding target component is sandwiched from both front and rear sides thereof on both sides of the welded portion.

According to these aspects, both sides of the welded portion of the welding target component are held by the plurality of belts. Thus, the welding target component can be prevented from expanding/contracting or moving in a direction orthogonal to the supplying direction of the welding target component. Therefore, the welding position can be accurately held in the direction orthogonal to the supplying direction. Particularly, the respective aspects are effective when elastic members are attached on the welding target component under a stretched state in the direction orthogonal to the supplying direction.

In addition, both side portions of the welded portion of the welding target component can be prevented from unexpectedly appearing in a image pick-up range when the method further comprises an image pick-up step of picking up an image of the welded portion in a state in which the sandwiching of the welding target component by the plurality of belts is maintained and when the welding device further comprises an image pick-up member that picks up an image of the welded portion of the thermoplastic sheets in a state in which the welding target component is sandwiched by the plurality of belts. Therefore, determination (for example, determination as to whether the welding has been successfully performed) or the like using the result of picking up an image of the welded portion can be accurately performed.

Note that the disposable worn article can be used, although not being limited, as a worn target component so long as it has a diaper main body that extends from the front belly part to the back part via the crotch part of a wearer and four side panel pieces each of which extends from both front and rear end portions of the diaper main body to both right and left sides so as to cover the side surfaces of the lumbar part of the wearer when the disposable worn article is worn.

In this case, the welding step welds two side panel pieces, which face each other on the right side of the diaper main body, to each other and welds two side panel pieces, which face each other on the left side of the diaper main body, to each other in a state in which the diaper main body is folded in half. Thus, the disposable diaper can be produced.

In addition, the anvil and the horn is employed that weld two side panel pieces, which face each other on the right side of the diaper main body, to each other and weld two side panel pieces, which face each other on the left side of the diaper main body, to each other in a state in which the diaper main body is folded in half. Thus, the side panel pieces of the disposable diaper can be welded to each other.

Moreover, other examples of the disposable worn article according to the present invention include, for example, sanitary napkins that hold an absorber between a pair of thermoplastic sheets, nonwoven gowns (operating gowns), or the like.

The invention claimed is:

1. A method for producing a disposable worn article in which a welding target component having facing portions is continuously welded with a predetermined pattern in a range from one end portion to the other end portion of the facing portions, the facing portions being two mutually-facing portions constituted by thermoplastic sheets, the method comprising:
a rotating step of rotating an anvil about a predetermined rotating shaft, the anvil having a welding surface for continuously welding the facing portions to each other with the predetermined pattern between the welding surface and a horn for applying ultrasonic vibrations to the facing portions; and
a welding step of intermittently supplying, in a state in which the anvil is rotated, a plurality of the welding target components to a place between the welding surface of the anvil and the horn to continuously weld the facing portions to each other with the predetermined pattern in each of the welding target components, wherein
the welding surface of the anvil is provided over a whole circumference about the rotating shaft such that an interval between the welding surface of the anvil and the horn is maintained at an interval at which the facing portions are continuously weldable to each other with the predetermined pattern regardless of a rotating position of the anvil in the rotating step the horn has an oscillating surface that applies ultrasonic vibrations to the facing portions and extends in a tangential direction to the welding surface of the anvil, and the method for producing the worn article further comprises an adjustment step of adjusting, when a portion of the oscillating surface facing the welding surface of the anvil is degraded, a positional relationship between the horn and the anvil by shifting the horn in the tangential direction such that a portion other than the degraded portion of the oscillating surface faces the anvil.

2. The method for producing the disposable worn article according to claim 1, wherein
the welding step supplies the facing portions to the place between the welding surface of the anvil and the horn in a state in which the welding target component is sandwiched from both front and rear sides thereof by a plurality of belts on both sides of the welded portion.

3. The method for producing the disposable worn article according to claim 2, further comprising:
an image pick-up step of picking up an image of the welded portion in a state in which the sandwiching of the welding target component by the plurality of belts is maintained.

4. The method for producing the disposable worn article according to claim 1, wherein
the welding target component has a diaper main body that extends from a front belly part to a back part via a crotch part of a wearer and four side panel pieces each of which extends from both front and rear end portions of the diaper main body to both right and left sides of the diaper main body so as to cover side surfaces of a lumbar part of the wearer when the disposable worn article is worn, and
the welding step welds two side panel pieces, which face each other on the right side of the diaper main body, to each other and welds two side panel pieces, which face each other on the left side of the diaper main body, to each other in a state in which the diaper main body is folded in half.

* * * * *